United States Patent [19]

Anderson et al.

[11] 4,088,699
[45] May 9, 1978

[54] PRODUCTION OF ARALKYL TERTIARY HYDROPEROXIDES

[75] Inventors: John E. Anderson, Houston, Tex.; Ward J. Burkholder, Baton Rouge, La.

[73] Assignee: The Goodyear Tire & Rubber Company, Akron, Ohio

[21] Appl. No.: 462,596

[22] Filed: Apr. 22, 1974

Related U.S. Application Data

[63] Continuation-in-part of Ser. No. 285,481, Aug. 31, 1972, abandoned.

[51] Int. Cl.² .............................................. C07C 179/02
[52] U.S. Cl. ............................. 260/610 B; 260/610 A
[58] Field of Search ......................... 203/89; 202/236; 260/610 B, 610 A; 284/481

[56] References Cited

U.S. PATENT DOCUMENTS 2,856,432  10/1958  Conner et al. .................. 260/610 A
2,856,433  10/1958  Thompson ...................... 260/610 A
3,092,587  6/1963   Ester et al. ..................... 252/426
3,620,283  11/1971  Brown .............................. 159/13

Primary Examiner—James O. Thomas, Jr.
Assistant Examiner—Werren B. Lone
Attorney, Agent, or Firm—Browning, Bushman & Zamecki

[57] ABSTRACT

A portion of a stream obtained by the oxidation of an aryl tertiary alkane and containing primarily aralkyl tertiary monohydroperoxide, substantial amounts of aryl tertiary alkane, smaller amounts of keto aryl tertiary alkanols, aralkyl tertiary dialkanols and other by-products is subjected to a separation step wherein a fraction containing the greater part of the aryl tertiary alkane and at least some of the monohydroperoxide, and a fraction containing the keto aryl tertiary alkanol are separated from one another and the fraction containing the aryl tertiary alkane and the monohydroperoxide is returned to the oxidation reaction.

19 Claims, 1 Drawing Figure

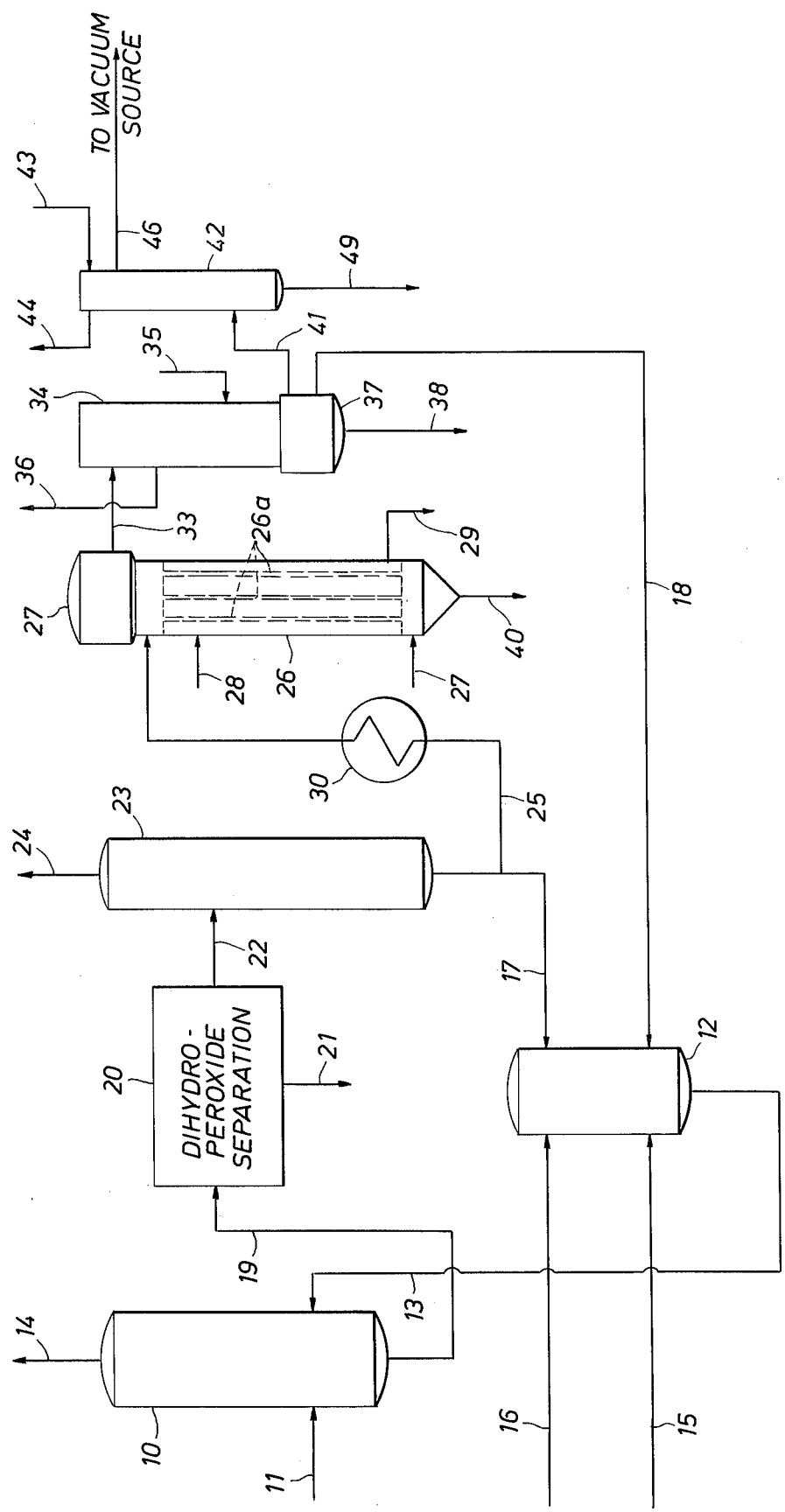

PRODUCTION OF ARALKYL TERTIARY HYDROPEROXIDES

CROSS REFERENCE TO RELATED APPLICATION

This application is a continuation-in-part application of Ser. No. 285,481, filed Aug. 31, 1972 now abandoned.

BACKGROUND OF THE INVENTION

The present invention relates to the production of aralkyl tertiary hydroperoxides and more particularly to the production of p-diisopropylbenzene dihydroperoxide.

In the production of aralkyl tertiary polyhydroperoxides such as, for example, p-diisopropylbenzene dihydroperoxide, there is also produced the corresponding monohydroperoxide. Indeed, the rate of formation of the monohydroperoxide is approximately proportional to the concentration of the aryl tertiary alkane in the reaction mixture and that of the dihydroperoxide to the concentration of the monohydroperoxide. The reaction, however, comes to a virtual standstill before all of the monohydroperoxide is converted to the dihydroperoxide and consequently for a given amount of the aryl tertiary alkane only a small proportion of the dihydroperoxide is obtained.

It is known that the oxidation reaction can be conducted so as to yield a considerably higher amount of the aralkyl tertiary dihydroperoxide if the dihydroperoxide is separated from the oxidation reaction mixture alternately or concurrently with the oxidation reaction while the oxidation is continued with the remaining reaction mixture. As a practical matter, in a continuous reaction, the dihydroperoxide is continuously removed from the reaction mixture and the remaining portion of the oxidation reaction product is recycled to the oxidation reaction to convert the large amounts of monohydroperoxide present in the recycle stream to dihydroperoxide.

Unfortunately, the oxidation reaction product from which the dihydroperoxide has been removed and which is recycled to the oxidation reaction, in addition to containing large amounts of the monohydroperoxide and unreacted aryl tertiary alkane, also contains undesirable by-products and impurities which are quite detrimental to the efficiency of the oxidation reaction. For example, it is known that in such reactions keto aryl tertiary alkanols, aralkyl tertiary dialkanols and other by-products are are also produced. These materials, particularly the keto aryl tertiary alkanols hinder the oxidation reaction. As a consequence of the above-described recycle of the dihydroperoxide free oxidation reaction product to the oxidation reactor, these impurities and by-products continue to build up to the point where, if the oxidation reaction is to be conducted efficiently and economically, it may become necessary to completely discharge the reactor contents and charge the reactor with fresh reactants. Such a solution is both expensive and time consuming.

SUMMARY OF THE INVENTION

It is, therefore, an object of the present invention to provide an improved process for the production of aralkyl tertiary polyhydroperoxides.

It is a further object of the present invention to increase the efficiency of the oxidation of an aryl tertiary alkane to an aralkyl tertiary polyhydroperoxide.

Still another object of the present invention is to provide a process for treating an oxidation reaction product obtained by the oxidation of an aryl tertiary alkane with an oxygen containing gas.

An important object of the present invention is to provide a process for the oxidation of an aryl tertiary alkane to an aralkyl tertiary dihydroperoxide in which the oxidation reaction is maintained under basically steady state conditions.

These and other objects of the present invention will become apparent from the drawing, the description given herein and the appended claims.

Generally speaking, the process of the present invention comprises a novel method of treating an oxidation reaction product obtained by oxidizing an aryl tertiary alkane with an oxygen containing gas at elevated temperatures. In such a process, aralkyl tertiary polyhydroperoxide, aralkyl tertiary monohydroperoxide, keto aryl tertiary alkanols, aralkyl tertiary dialkanols and numerous other products are produced. According to the process of the present invention, the greater part of the polyhydroperoxide, the desired product, is separated from the oxidation reaction mixture and the remaining portion of the oxidation reaction mixture is recycled to the oxidation reaction. In the co-pending application referenced above, a portion of the recycled stream was, preferably concurrently, removed and sent to a separation zone and separated into a first fraction containing the greater part of the monohydroperoxide and a second fraction containing the greater part of the keto aryl tertiary alkanol. It has now been found that whereas it is preferable, as described in the aforementioned co-pending application, that the first fraction contain the greater part of the monohydroperoxide present in the portion sent to the separation zone, advantageous results are obtained if the separation zone is operated such that the first fraction contains the greater part of the unreacted aryl tertiary alkane and at least some of the monohydroperoxide, the second fraction containing the greater part of the keto aryl tertiary alkanol. Preferably, the first fraction, containing the monohydroperoxide and the aryl tertiary alkane, is returned to the oxidation reaction.

BRIEF DESCRIPTION OF THE DRAWINGS

The single FIGURE is a diagrammatic representation of the process of the present invention.

DESCRIPTION OF THE PREFERRED EMBODIMENT

The process which is the subject of the present invention involves the production of aralkyl tertiary hydroperoxides which are obtained by the oxidation of an alkyl aromatic hydrocarbon and more specifically a aryl tertiary alkane which may contain other substituents. The term aryl tertiary alkane as used herein and from which the hydroperoxides are obtained is intended to include compounds defined by the formulas:

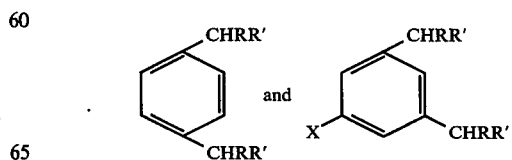

wherein R and R' may be the same or different and are alkyl or cycloalkyl and X is one of the group, hydrogen, lower alkyl, —CHRR', halogen and —NO$_2$. The alkyl radical may be straight chain or branched chain but preferably is straight chain having 1-2 carbon atoms. Non-limiting examples of such compounds include m- and p-diisopropylbenzene, m- and p-di-sec-butylbenzene, ispropyl-4-sec-butylbenzene, isopropyl-3-sec-butylbenzene, 1, 3, 5-triisopropylbenzene, 3, 5-diisopropyltoluene, 3, 5-diisopropylchlorobenzene and 3, 5-diisopropylnitrobenzene and the like. The oxidation of the above described aryl tertiary alkanes results in the formation of aralkyl tertiary hydroperoxides having the formulas:

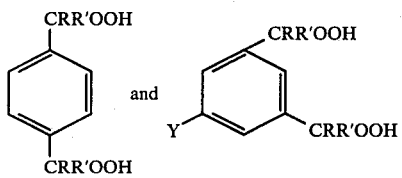

wherein R and R' have the same significance as in the previously described formulas for the aryl tertiary alkanes but wherein Y can also be —CRR'OOH as well as the above-named groupings for X. Non-limiting examples of such aralkyl tertiary hydroperoxides include m- and p-α, a, a', a'-tetramethyl-xylylene dihydroperoxide, m- and p-α, methyl, a ethyl, a' methyl, a'-ethyl xylylene dihydroperoxide 1, 3, 5-triisopropylbenzene dihydroperoxide, 3, 5-diisopropyltoluene dihydroperoxide, 3, 5-diisopropylchlorobenzene dihydroperoxide, 3, 5-diisopropylnitrobenzene dihydroperoxide and the like, the designation a referring to the Greek letter alpha.

The oxidation reaction is generally carried out in the liquid phase in the presence of an oxygen containing gas which, of coure, may be pure oxygen or a gaseous mixture containing oxygen, such as air, and may with advantage include suitable proportions of ozone. It is generally preferred in the oxidation reaction to adjust the reaction parameters and the quantity of oxygen containing gas in such a way that an excess of oxygen over that absorbed by the reaction mixture is introduced therein. Such an excess may vary over wide limits but is has generally been found that an excess of at least 10% is preferred.

While not absolutely necessary, it is preferable to perform the oxidation reaction in the presence of alkali substances such as oxides or hydroxides of the alkali and/or alkaline earth metals, or their salt with weak inorganic or organic acids such as the carbonates, bicarbonates and acetates or in the presence of other basic substances such as ammonia. The presence of the basic materials in the oxidation reactions retards the development of excessive acidity due to the formation of carboxylic acids which, in turn, hinder the oxidation reaction.

The oxidation reaction may be conducted over a wide range of temperatures as for example from 50°-150° C. When the reaction is conducted in the homogeneous phase suitable temperatures will range from between 70°-120° C and more preferably, between 80° and 110° C at ambient pressures. Under heterogeneous conditions, as, for example, in the presence of water, temperatures between 85° and 100° C and preferably around 90° C have been found to be suitable at ambient pressure.

The oxidation reaction may be conducted at atmospheric or super-atmospheric pressure, with consequent broadening of the temperature range or it may be conducted at sub-atmospheric pressure.

As noted, when an oxidation reaction of the type under consideration is continued for a protracted time such as occurs in a continuous process, the rate of production of the dihydroperoxide on the basis of a constant reaction volume decreases progressively. This is due to the build up in the oxidation reaction product of undesirable by-products such as keto aryl tertiary alkanols, as, for example, m-or p-acetyl-2-hydroxy isopropylbenzene alkanols, aralkyl tertiary dialkanols and other, usually higher boiling, materials. The resulting fall in rate of the oxidation reaction, although slow, ultimately makes it necessary to stop the oxidation and to remove, in one way or another, the interfering products. Complete cessation of the reaction is economically undesirable and consequently is to be avoided if at all possible.

In the typical process for the production of dihydroperoxides, the oxidation reaction product is treated to remove the dihydroperoxide. This can be accomplished by techniques well known in the art. For example, processes for separating dihydroperoxides from the oxidation reaction mixture are disclosed in U.S. Pat. Nos. 2,856,432; 3,190,924; 2,856,433 and 3,190,923.

The portion of the oxidation reaction mixture remaining after the polyhydroperoxide has been removed is rich in the corresponding monohydroperoxide and unreacted aryl tertiary alkane and contains lesser amounts of the impurities noted above, i.e. the keto aryl tertiary alkanols, the aralkyl tertiary dialkanols and the like. It is to the treatment of this latter portion of the oxidation reaction mixture to which this process is directed.

By utilizing the process of the present invention, the recycle of the portion of the oxidation reaction mixture, substantially free of the polyhydroperoxide, to the oxidation reaction does not result in the continuous build up of unwanted impurities and by-products which decrease the efficiency of the oxidation reaction and accordingly lower the overall yield of the polyhydroperoxide.

To more fully explain the invention, reference is made to the accompanying FIGURE. While the process, as noted above, is applicable to the production of numerous aralkyl tertiary polyhydroperoxides produced from a wide variety of aryl tertiary alkanes, the invention will be described with particular reference to the production of p-dissopropylbenzene dihydroperoxide produced from the liquid phase oxidation of p-diisopropylbenzene in the presence of a diluted aqueous caustic solution. Referring then to the drawing, an oxygen containing gas, via line 11, enters reactor 10, operated at an elevated temperature. A reactor feed stream passing from recycle tank 12 via line 13 also enters reactor 10 where it is admixed with the oxygen containing gas. Gases liberated from reactor 10 are vented via line 14. The feed to recycle tank 12 comprises fresh p-diisopropylbenzene entering via line 15, a dilute caustic stream entering via line 16 and several recycle streams entering via lines 17 ahd 18. The nature of the streams in the latter lines will be discussed hereafter.

The oxidation reaction effluent containing unreacted p-diisopropylbenzene, p-diisopropylbenzene dihydroperoxide, p-diisopropylbenzene monohydroperoxide, p-acetyl-a-hydroxy isopropylbenzene, p–a, a'-dihydroxy diisopropylbenzene and other impurities is removed from reactor 10 through line 19 and is sent to a dihydroperoxide recovery unit 20. As noted above, the recovery of the dihydroperoxide may be accomplished by numerous means. The dihydroperoxide thus recovered is sent for further purification and processing via line 21.

The oxidation reaction mixture, free of the greater portion of the dihydroperoxide, passes through line 22 into a distillation zone 23 wherein the bulk of any light materials such as benzene, toluene, xylene or other light hydrocarbon which may have been used in the dihydroperoxide separation are removed and taken overhead through line 24. The bottoms from distillation zone 23 containing most of the unreacted p-diisopropylbenzene, (p-DIPB) p-diisopropylbenzene monohydroperoxide (p-MOX), p-acetyl-a-hydroxy isopropylbenzene (p-AIPOL), p-a a'-dihydroxy diisopropylbenzene other by-products and a small amount of the dihydroperoxide (p-DIX) leaves as a heavier fraction and is sent to recycle tank 12 via line 17.

A portion of the recycle stream passing via line 17 into tank 12 is concurrently removed via line 25 and sent thru preheater 30 to evaporator-stripper 26. In the particular embodiment shown, evaporator-stripper 26 comprises a falling film evaporator employing sparging or stripping stream entering the lower portion thereof via line 27. The shell side of evaporator stripper 26 is heated to the desired temperature by steam entering via line 28 and exiting via line 29. As the liquid charge entering evaporator-stripper through line 25 flows in a thin film down the wall of tubes 26a of evaporator-stripper 26, it is contacted by the sparging or stripping stream entering via line 27 and passing upwardly thru tubes 26a. The lighter components of the charge entering via line 25, i.e. any residual benzene, p-diisopropylbenzene, p-diisopropylbenzene monohydroperoxide and any other light components are taken overhead together with the stripping steam into disengaging drum 27 where any entrained liquid is separated from the vapor and returned to evaporator-stripper 26. A heavy bottoms fraction is removed from evaporator stripper 26 thru line 40 and sent to waste disposal or further processing if desired. Vapors from disengaging drum 27 pass through line 33 into overhead condenser 34 which is cooled by water entering via line 35 and leaving via line 36. The condensed vapors are collected in overhead receiver 37, where they separate into a hydrocarbon phase and a water phase, the water phase being removed via line 38, the hydrocarbon phase being removed via line 18 and passed to recycle tank 12 from whence it ultimately flows into reactor 10.

Light ends and non-condensibles from receiver 37 are removed through line 41 and drawn into vent condenser 42, cooled by chilled water entering via line 43 and exiting via line 44. Any condensate in condenser 42 is removed thru line 49 for further processing while non-condensibles pass thru line 46. A source of vacuum via line 46 serves to maintain sub-atmospheric conditions in evaporator-stripper 26, disengaging drum 27, overhead condenser 34, receiver 37 and vent condenser 42. Such a vacuum source can range from a simple vacuum pump to steam jet ejectors which can be single or multiple stage.

The process of the present invention has been described in connection with the use of an evaporator-stripper operated under vacuum conditions as the separation means. However, it is to be understood that the process of the present invention does not reside in the use of any particular separating technique albeit that separating techniques employing evaporative-stripping lend themselves especially well to the process. In general, any separating technique wherein a heat sensitive material may be separated into fractions of higher and lower volitility can be employed. Accordingly, a wide variety of other separating techniques or means may be utilized as, for example, simple heat exchangers, evaporators, reactors, thin film strippers, distillation columns, wiped surface heat exchangers, or the like. Particularly desirable separating means comprise evaporator-stripper systems such as falling film evaporators or gravity fed cascade-type tube and disc strippers.

While, as explained above, other means of separation can be employed in carrying out the process of the present invention, it is preferred that the separator zone employ an evaporative type separator such as an evaporator-stripper. Operating variables in the separation zone of the process herein will, of course, depend upon the precise materials being dealt with and the separation technique employed, it being understood that the components which are the subject of the process of the present invention are, in general, heat sensitive and will decompose under certain time-temperature conditions. It has been found that to optimize recovery of the monohydroperoxide in the first fraction, i.e. the more volatile fraction being recovered from the separation zone, that the bottoms temperature, when the preferred evaporator-stripper is used, should be maintained between 210° and 275° F. and preferably between about 250° to about 270° F. As noted, excessive bottoms temperature and residence time should be avoided since the materials being dealt with will decompose, possibly in an explosive manner.

The feed temperature, i.e., the temperature of the material being fed to the separation zone will likewise depend upon the precise separation technique and the composition of the feed stream but in general will, when evaporative-stripping is used, range from about 80° to about 275° F. and more preferably from about 180° to about 270° F., the latter temperature range being particularly desirable when p-diisopropylbenzene dihydroperoxide is the polyhydroperoxide being produced.

When evaporative-stripping is used as the separating technique, an inert stripping medium which will enhance the vaporization of the more volatile components without any deleterious side reactions should be employed. Numerous inert stripping mediums can be employed as, for example, steam, nitrogen, helium, argon, air, carbon monoxide, carbon dioxide, certain fuel and combustion gases, hydrogen, inert hydrocarbons as, for example, methane, ethane, butane, pentane, fluorocarbons such as the Freons as, for example, fluoro and fluoro-chloro substituted methane, ethane, propane, etc., and mixtures thereof. Preferably, because of its ready availability and low cost, the stripping medium of choice is steam.

The ratio of the sparge or stripping medium to the feed being introduced into the evaporator-stripper will vary depending upon the stripping medium employed, the desired amount of overhead recovery and the operating pressure of the process. For example, in the case of the recovery of p-diisopropylbenzene monohydroperoxide, when steam is employed as the stripping medium, higher sparge steam to feed ratios result in higher monohydroperoxide recovery in the overhead. In general, when steam is employed as the stripping medium, a sparge steam to feed ratio of from about 2/1 to about 0.3/1 and more preferably from about 1.5/1 to about 0.5/1 will be employed, the ratios being on a weight to weight basis.

The separation can be conducted at atmospheric, subatmospheric or super-atmospheric pressures depending on what technique is used. When an evaporator-stripper is employed, the separation will usually be conducted at sub-atmospheric pressure. It is to be understood that, even in such cases, atmospheric and super-atmospheric pressures can be employed, the result, of course, being that higher operating temperatures and higher stripping medium to feed ratios must be employed in order to maintain adequate recovery of the monohydroperoxide in the overhead fraction. On the other hand, attempts to operate at pressures too low may result in partial condensation of the overhead vapors which again will lessen the recovery of the monohydroperoxide. In general, when an evaporator-stripper system such as that described above is employed in the separation technique, sub-atmospheric pressures ranging from about 30 to about 150 mm of Hg and preferably from about 40 to about 115 mm of Hg will be employed.

As explained above, the process of the present invention is characterized by the fact that only a portion of the oxidation reaction product remaining after the dihydroperoxide has been substantially removed is processed in the separation step. The portion of the substantially polyhydroperoxide free oxidation reaction product (recycle stream) which is processed in the separation step will, of course, depend on its composition. However, in general, the portion of the recycle stream which is processed in the separation zone will range from about 0.01 to about 20% by weight and more particularly from about 1 to about 10% by weight of the total recycle stream, i.e. the oxidation reaction product free of the greater part of the dihydroperoxide.

In the system discussed above, a generally conventional distillation zone depicted by column 23 is shown for the purpose of separating the bulk of any light organic materials such as benzene which might be present. As noted, these materials may be introduced in the dihydroperoxide recovery step and would preferably be largely removed prior to recycle of the dihydroperoxide free reaction product back to the oxidation reactor. It is to be understood, however, that column 23 can be dispensed with if no such prior removal of light ends is required. Moreover, even if such light ends were present, column 23 may still be dispensed with, the result being that the more volatile fractions from the separation zone would contain much higher quantities of such lighter components, i.e. benzene or the like, assuming proper process conditions.

While the process was described above as being operated in a generally continuous manner, it is to be understood that batchwise operation is within the scope of the present invention. Also, while a single separation zone is depicted, multiple separation stages are contemplated as well.

To more fully illustrate the present invention the following non-limiting examples are presented:

EXAMPLE I

A separating system basically the same as that shown in the accompanying diagram was employed. The evaporator-stripper used was a falling film evaporator of the shell and tube design.

The evaporator-stripper was operated under the following conditions:

| | |
|---|---|
| Feed Temperature | 265° F. |
| Bottoms Temperature | 270° F. |
| Superheated Sparge-Stripping Steam/Feed Ratio (wt./wt.) | 1.16/1.0 |
| Tube Side Operating Pressure | 110 mm of Hg |

The shell side of the evaporator-stripper was heated with steam at 65 psig and 310° F.

The following table presents design data showing the composition of the feed to the evaporator-stripper, i.e. the stream passing via line 25, the overhead organic layer, i.e. the stream being recycled via line 18 and the bottoms stream from the stripper, i.e. the stream being removed via line 40.

| | Feed Wt. % | Overhead Wt. % | % Recovery | Bottoms Wt. % |
|---|---|---|---|---|
| Benzene | 5.0 | 6.3 | 100.0 | — |
| p-DIPB | 25.0 | 31.8 | 100.0 | — |
| p-MOX | 45.0 | 47.3 | 82.5 | 37.0 |
| p-DIX | 4.0 | 0.1 | 2.9 | 18.2 |
| p-AIPOL | 5.0 | 1.6 | 25.0 | 17.6 |
| Others | 16.0 | 12.9 | 63.7 | 27.2 |
| | 100.0 | 100.0 | | 100.0 |

As can be seen from the data, all of the light ends, i.e. the benzene and the p-DIPB, are recovered in the more volatile or overhead fraction. Moreover, the bulk of the p-MOX, the valuable recycle precursor is also recovered in this fraction. As can further be seen from observing the data, the greatest part of the interfering impurities, i.e. p-AIPOL and the other heavier materials are rejected from the bottom of evaporator-stripper 26 and are removed via line 40. As was earlier mentioned, it is these impurities, particularly the p-AIPOL, which are the greatest cause of loss of efficiency in the oxidation reaction.

EXAMPLE II

The effect of employing the above-described and examplified process is best seen by a comparison of the operation of the oxidation reaction operated in the absence of the process of the present invention (Case I) and operated employing the process of the present invention (Case II).

| Oxidizer Conditions | Case I | Case II |
|---|---|---|
| Residence Time, hrs. | 1.333 | 1.333 |
| Temperature, ° F. | 235 | 230 |
| pH | 6.5 | 6.5 |
| Flows to Oxidizer (wt. units/day) | | |
| p-DIPB | 45.3 | 47.2 |
| $O_2$ | 14.0 | 16.5 |
| Production (wt. units/day) | | |
| p-DIX | 25.6 | 32.9 |
| Yield: (p-DIPB to p-DIX) | | |
| Entire Unit, % | 42.5 | 49.0 |

As can be seen from an analysis of the data in the above table, the process of the present invention affords a marked increase in the production of p-DIX. As can further be seen, the use of one embodiment of the process of the present invention, in effect, results in a "bigger reactor" in that more p-DIPB and oxygen can be fed to the reactor employing the process of the present invention. The third point which is, of course, quite important is that the overall efficiency of the oxidizer is markedly increased employing the process disclosed herein. Note, for example, that employing the conventional process, the yield is 42.5% whereas employing the process of the present invention, the yield increases to 49.0%.

EXAMPLE III

In this example, the separating system was basically the same as that shown in the accompanying diagram and employed in obtaining the data in Example I except that the evaporator-stripper was operated under conditions such that the overhead, i.e. the first fraction, did not contain the greater part of the p-MOX fed to the stripper. The compositional breakdown of the feed to the stripper and the overhead and the bottoms fraction from the stripper for two sets of operating conditions are given below:

| 1 | |
|---|---|
| Feed Temperature | 220° F. |
| Bottoms Temperature | 210° F. |
| Superheated Sparge-Stripping Steam/Feed Ratio (wt/wt) | 1.82/1 |
| Tube Side Operation Pressure | 95 mm of Hg |

The shell side of the evaporator-stripper was heated with steam at 10 psig.

| | Feed | Overhead | | Bottoms |
|---|---|---|---|---|
| | Wt. % | Wt. % | % Recovery | Wt. % |
| Benzene | 4.6 | 8.3 | 100.0 | — |
| p-DIPB | 25.7 | 45.8 | 99.0 | 0.6 |
| p-MOX | 39.8 | 31.5 | 44.0 | 50.2 |
| p-DIX | 6.9 | 0.5 | 3.8 | 14.9 |
| p-AIPOL | 4.3 | 1.1 | 14.1 | 8.3 |
| Others | 18.7 | 12.8 | 38.3 | 26.0 |
| | 100.0 | 100.0 | | 100.0 |

| 2 | |
|---|---|
| Feed Temperature | 220° F. |
| Bottoms Temperature | 220° F. |
| Superheated Sparge-Stripping Steam/Feed Ratio (wt/wt) | 1.95/1 |
| Tube Side Operating Pressure | 95 mm of Hg |

The shell side of the evaporator-stripper was heated with steam at 10 psig.

| | Feed | Overhead | | Bottoms |
|---|---|---|---|---|
| | Wt. % | Wt. % | % Recovery | Wt. % |
| Benzene | 8.8 | 16.4 | 100.0 | — |
| p-DIPB | 24.4 | 43.7 | 95.7 | 2.2 |
| p-MOX | 39.2 | 26.8 | 36.4 | 53.7 |
| p-DIX | 6.5 | 0.3 | 2.6 | 13.6 |
| p-AIPOL | 4.8 | 1.4 | 15.9 | 8.6 |
| Others | 16.3 | 11.4 | 37.4 | 21.9 |
| | 100.0 | 100.0 | | 100.0 |

As previously noted, the advantages of the process of the present invention can be realized without the necessity for separating into the overhead or first fraction the greater part of the monohydroperoxide (p-MOX) contained in the portion of the recycled stream sent to the separation zone. In both cases above, the amount of p-MOX in the bottoms is greater than that in the overhead. Nonetheless, the greater part of the interfering impurities, i.e. p-AIPOL and the other heavier materials are rejected from the bottom of the evaporator-stripper 26 and are removed via line 40. It has been found that when the evaporator-stripper is operated under conditions such as those shown above, i.e. such that at least some of the monohydroperoxide in the portion of the recycled stream sent to the separation zone is recovered in the overhead or first fraction and the greater part of the aforementioned impurities are removed with the second fraction, the efficiency of the oxidizer is maintained and the yield of the dihydroperoxide based on aryl tertiary alkane, i.e. p-DIPB, is increased.

Ideally, rejection of all of the keto aryl tertiary alkanols and other such impurities which hinder the oxidation reaction into the bottoms or second fraction, and maximum recovery of the monohydroperoxide along with the aryl tertiary alkane, i.e. the DIPB, in the first fraction is desirable. Such would result in maximizing steady state operation of the oxidizer by purging from the system those impurities which upset the oxidation reaction, but ensure that none of the valuable precursor, i.e. the monohydroperoxide, is lost. As a practical matter, complete rejection of the interfering impurities results in substantial losses of the valuable precursor, i.e. the monohydroperoxide, and, accordingly, the process is conducted such that at least the greater portion of such impurities, e.g. the keto aryl tertiary alkanols, are removed in the second fraction, some of the monohydroperoxide being recovered in the first or overhead fraction.

We claim:

1. In a process for the production of an aralkyl tertiary polyhydroperoxide selected from the class consisting of

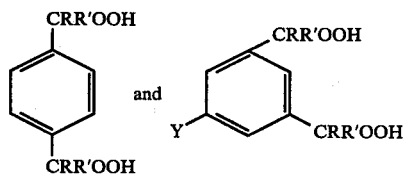

and wherein R and R' are alkyl radicals having 1-2 carbon atoms and Y is selected from the class consisting of hydrogen, —CHRR', lower alkyl -CRR'OOH, halogen and —NO₂ by the oxidation of an aryl tertiary alkane selected from the class consisting of

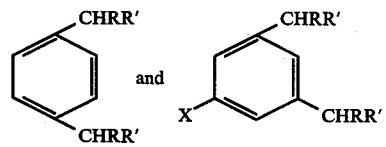

and wherein X is selected from the class consisting of hydrogen, —CHRR', lower alkyl, halogen and —NO₂ with an oxygen containing gas at temperatures in the range of 50° - 150° C wherein there are produced, in addition to said aralkyl tertiary polyhydroperoxide, a corresponding aralkyl tertiary monohydroperoxide, a corresponding keto aryl tertiary alkanol, and a corresponding aryl tertiary dialkanol, and wherein the greater portion of said polyhydroperoxide is separated from the oxidation reaction product and a resultant recycle stream containing unreacted aryl tertiary alkane and aralkyl tertiary monohydroperoxide is returned to the oxidation reaction, the improvement comprising:

(a) introducing a portion of said recycle stream into an evaporative-stripper zone employing an inert stripping medium, said stripper medium being of a nature which enhances the removal of said aryl tertiary alkane and aralkyl tertiary monohydroperoxide from said portion of said recycle stream without undergoing deleterious side reactions, (b) separating, in said evaporative-stripping zone, said portion of said recycle stream into a first fraction containing the greater part of said aryl tertiary alkane and at least some of said monohydroperoxide contained in said portion of said recycle stream and a second fraction containing the greater part of said keto aryl tertiary alkanol, and (c) returning said first fraction to said oxidation reaction.

2. The process of claim 1 wherein said first fraction contains the greater part of said monohydroperoxide contained in said portion of said recycle stream.

3. The process of claim 1 wherein said evaporative-stripping is carried out by falling film evaporation.

4. The process of claim 3 wherein said inert stripping medium comprises steam.

5. The process of claim 3 wherein said falling film evaporation is conducted at sub-atmospheric pressure.

6. The process of claim 4 wherein said inert strippng medium comprises steam and the weight ratio of the stripping steam to the portion of said recycle stream is from about 2 to 1 to about 0.3 to 1.

7. The process of claim 6 wherein said falling film evaporation is conducted at a temperature of from about 210 to about 275° F.

8. The process of claim 7 wherein said falling film evaporation is conducted at a pressure of from about 30 to about 150 millimeters of Hg.

9. The process of claim 1 wherein said aryl tertiary alkane comprises p-diisopropylbenzene, said aralkyl tertiary polyhydroperoxide comprises p-diisopropylbenzene dihydroperoxide, said aralkyl tertiary monohydroperoxide comprises p-diisopropylbenzene monohydroperoxide, said keto aryl tertiary alkanol comprises p-acetyl-a-hydroxy isopropylbenzene and said aralkyl tertiary dialkanol comprises p-a, a'-dihydroxy diisopropylbenzene.

10. A process for treating an oxidation reaction product containing a polyhydroperoxide selected from the class consisting of

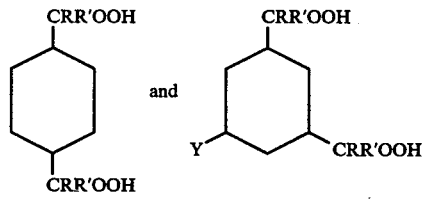

wherein R and R' are alkyl radicals having 1-2 carbon atoms and Y is selected from the class consisting of hydrogen, —CHRR', lower alkyl, —CRR'OOH, halogen and —NO$_2$ by oxidizing an aryl tertiary alkane selected from the class consisting of

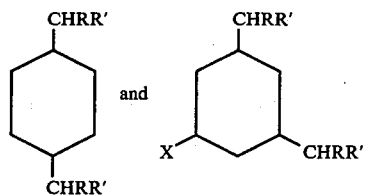

wherein X is selected from the class consisting of hydrogen, —CHRR', lower alkyl, halogen, and —NO$_2$, with an oxygen containing gas at temperatures in the range of 50° – 150° C comprising:

(a) separating from said oxidation reaction product the greater part of the aralkyl tertiary polyhydroperoxide produced and recovering a recycle stream containing said aryl tertiary alkane, a corresponding aralkyl tertiary monohydroperoxide, a corresponding keto aryl tertiary alkanol, and a corresponding aralkyl tertiary dialkanol.

(b) returning said recycle stream to the oxidation reaction, (c) introducing a portion of said recycle stream into an evaporative-stripping zone employing an inert stripping medium, said stripping medium being of a nature which enhances the removal of said aryl tertiary alkane and the corresponding aralkyl tertiary monohydroperoxide from said portion of said recycle stream without undergoing deleterious side reactions, (d) separating, in said evaporative-stripping zone, said portion of said recycle stream into a first fraction containing the greater part of said aryl tertiary alkane and at least some of said monohydroperoxide contained in said portion of said recycle stream, and a second fraction containing the greater part of said keto aryl tertiary alkanol, and (e) returning said first fraction to said oxidation reaction.

11. The process of claim 10 wherein said first fraction contains the greater part of said monohydroperoxide contained in said portion of said recycle stream.

12. The process of claim 10 wherein said evaporative-stripping is carried out by falling film evaporation.

13. The process of claim 12 wherein said inert stripping medium comprises steam.

14. The process of claim 10 wherein said falling film evaporation is conducted at sub-atmospheric pressure.

15. The process of claim 14 wherein said falling film evaporation is carried out in the presence of an inert stripping medium.

16. The process of claim 13 wherein said inert stripping medium comprises steam and the weight ratio of the stripping steam to the portion of said recycle stream is from about 2 to 1 to about 0.3 to 1.

17. The process of claim 12 wherein said falling film evaporation is conducted at a temperature of from about 210° to about 275° F.

18. The process of claim 17 wherein said falling film evaporation is conducted at a pressure of from about 30 to about 150 millimeters of Hg.

19. The process of claim 10 wherein said aryl tertiary alkane comprises p-diisopropylbenzene, said aralkyl tertiary polyhydroperoxide comprises p-diisopropylbenzene dihydroperoxide, said aralkyl teritary monohydroperoxide comprises p-diisopropylbenzene monohydroperoxide, said keto aryl tertiary alkanol comprises p-acetyl-a-hydroxy isopropylbenzene and said aralkyl tertiary dialkanol comprises p-a, a'dihydroxy diisopropylbenzene.

* * * * *